United States Patent
Mäki et al.

(10) Patent No.: US 7,766,162 B2
(45) Date of Patent: Aug. 3, 2010

(54) RECEPTACLE FOR A CATHETER

(75) Inventors: Thore Mäki, Skellefteå (SE); Urban Mäki, Linköping (SE)

(73) Assignee: Cimatex AB, Skellefteå (SE)

( * ) Notice: Subject to any disclaimer, the term of this patent is extended or adjusted under 35 U.S.C. 154(b) by 63 days.

(21) Appl. No.: 12/087,497

(22) PCT Filed: Dec. 21, 2006

(86) PCT No.: PCT/SE2006/050609
§ 371 (c)(1),
(2), (4) Date: Jul. 8, 2008

(87) PCT Pub. No.: WO2007/081264
PCT Pub. Date: Jul. 19, 2007

(65) Prior Publication Data
US 2009/0071851 A1 Mar. 19, 2009

(30) Foreign Application Priority Data
Jan. 10, 2006 (SE) .................................. 0600028

(51) Int. Cl.
*B65D 83/10* (2006.01)
*A61M 25/00* (2006.01)
*A61B 5/00* (2006.01)
(52) U.S. Cl. ................ 206/364; 206/63.3; 600/585
(58) Field of Classification Search ........... 206/63.3, 206/210, 364; 604/159, 170–171; 600/585
See application file for complete search history.

(56) References Cited

U.S. PATENT DOCUMENTS

| 4,160,451 A | 7/1979 | Chittenden |
| 4,903,826 A * | 2/1990 | Pearce ................. 206/63.3 |
| 4,921,096 A | 5/1990 | McFarlane |
| 5,125,416 A * | 6/1992 | Phillips ................ 600/585 |
| 5,344,011 A * | 9/1994 | DiBernardo et al. ...... 206/364 |
| 5,392,918 A | 2/1995 | Harrison |
| 5,730,150 A * | 3/1998 | Peppel et al. ........... 600/585 |
| 5,738,213 A * | 4/1998 | Whiting et al. .......... 206/364 |
| 5,769,222 A | 6/1998 | Banerian |
| 6,086,008 A | 7/2000 | Gray et al. |
| 7,191,900 B2 * | 3/2007 | Opie et al. ............ 206/364 |
| 7,234,597 B2 * | 6/2007 | Rowe et al. ............ 206/438 |
| 2002/0130059 A1 | 9/2002 | Armijo |
| 2004/0144667 A1 | 7/2004 | Duffy |

FOREIGN PATENT DOCUMENTS

| DE | 20009506 | 10/2001 |
| EP | 0820781 | 1/1998 |
| WO | 98/56687 | 12/1998 |
| WO | 01/78824 | 10/2001 |
| WO | 2004/022433 | 3/2004 |

* cited by examiner

*Primary Examiner*—Bryon P Gehman
(74) *Attorney, Agent, or Firm*—Dilworth & Barrese LLP

(57) ABSTRACT

A receptacle for a catheter, has a storage space (3) designed to receive a catheter, and an opening (4) connected to the storage space, through which opening a catheter in its longitudinal direction is pushable into and pullable out of the storage space (3). The receptacle (1) has a holding device (7) arranged in the storage space (3), which holding device is arranged to keep a catheter inserted into the storage space (3) in a spiral-shaped path under mutual separation of the different spiral turns of the spiral-shaped path so that the catheter is prevented from coming into contact with itself along the spiral-shaped path.

19 Claims, 3 Drawing Sheets

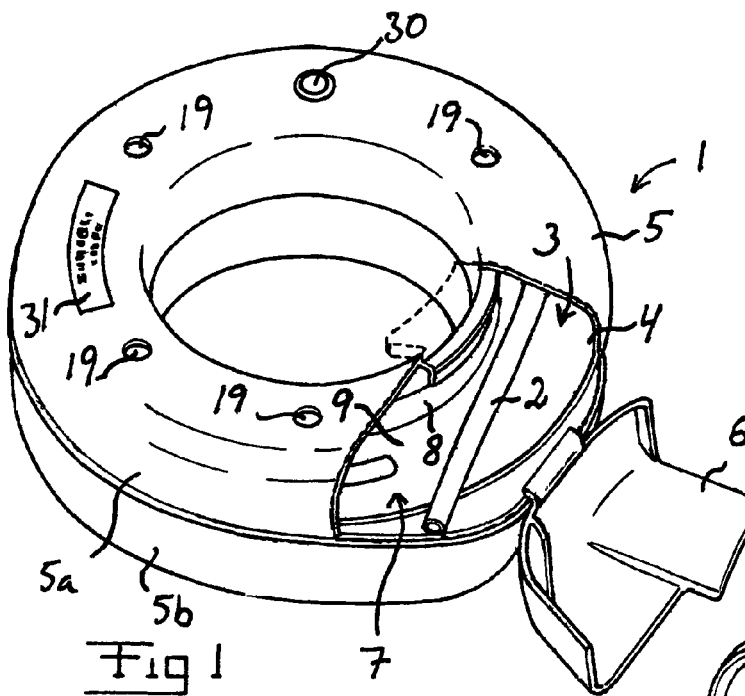
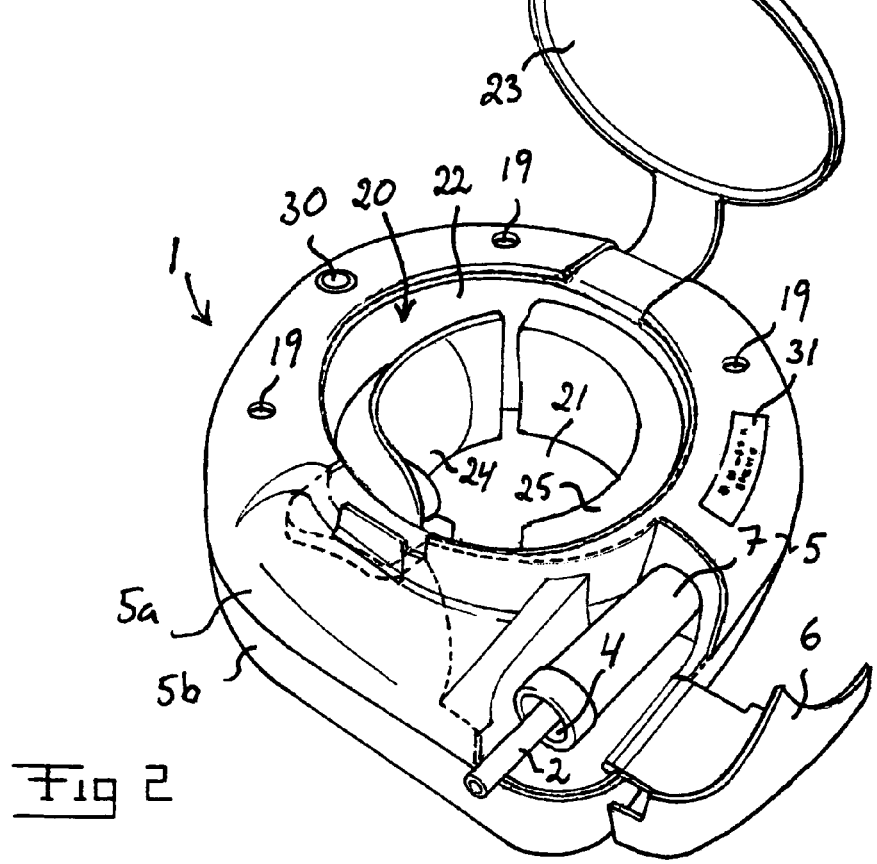
Fig 1
Fig 2

RECEPTACLE FOR A CATHETER

BACKGROUND OF THE INVENTION

Field of the Invention and Prior Art

The present invention relates to a receptacle for a catheter according to the description herein.

Disposable catheters, i.e. catheters that are used once and then disposed of, are today used in connection with catheterization. The catheters are stored in closed disposable packages before use. This results in an extensive material waste with respect to packages as well as catheters. A catheter is normally not destroyed when used and the disposable handling has merely hygienic and practical reasons. With conventional disposable packages of the above-mentioned type, the user should after performed catheterization dispose of the package and the used catheter in a suitable waste container, which may cause problems in the cases when a catheterization has to be performed at a place where such a waste container is not available. A solution to the last-mentioned problem is offered by a receptacle described in the document DE 200 09 506 U1, which receptacle is designed for storing a catheter before the use thereof and allows the catheter to be reinserted into the receptacle after use for storage until the used catheter is disposed of in a suitable waste container together with its receptacle. In the receptacle according to DE 200 09 506 U1, the catheter is stored reeled up on a rotatably arranged core of the receptacle.

OBJECT OF THE INVENTION

The object of the present invention is to provide a new type of storage receptacle for a catheter, which makes possible re-use of a catheter stored in the receptacle.

SUMMARY OF THE INVENTION

According to the invention, said object is achieved by a receptacle having the features defined herein.

The inventive receptacle comprises:

a storage space designed to receive a catheter, an opening connected to the storage space, through which opening a catheter in its longitudinal direction is pushable into and pullable out of the storage space, and a holding device arranged in the storage space, which holding device is arranged to keep a catheter inserted into the storage space in a spiral-shaped path under mutual separation of the different spiral turns of the spiral-shaped path so that the catheter is prevented from coming into contact with itself along the spiral-shaped path.

A catheter stored in the inventive receptacle can consequently be pulled out of the receptacle via said opening and after use be reinserted into the receptacle by being pushed back into the storage space through the opening. Due to the fact that the catheter is stored in a spiral-shaped path inside the receptacle, the receptacle may have a comparatively small size and a shape that makes possible a comfortable and user-friendly handling and storing of the receptacle. By means of the holding device, it is secured that the catheter will not come into contact with itself along the spiral-shaped path, whereby undesired bacterial growth on a used and into the receptacle reinserted catheter may be avoided. Practical tests with the inventive receptacle has shown that the bacterial growth hereby can be limited to such an extent that a safe re-use of a used and into the receptacle reinserted catheter will be possible if the catheter is rinsed out in flowing water or wiped off before the reinsertion into the receptacle, which would not have been possible without supplementary sterilization measures in case the catheter had been allowed to come into contact with itself after a reinsertion into a corresponding receptacle without a holding device of the type here in question. The possibility of re-use obtained by means of the inventive receptacle implies environmental advantages by the material saving associated therewith. The possibility of re-use also implies advantages for the user with respect to the handling, since the number of catheters that the user has to bring along, for instance when staying away from home, is reduced due to the fact that one and the same catheter can be used several times and thereby cover the needs for a longer time at the same time as a catheter that has been brought along can be stored in a safe and comfortable manner in the inventive receptacle.

According to an embodiment of the invention, the holding device is arranged to keep the catheter inserted into the storage space in a helicoidal path. Hereby, the storage space and thereby the entire receptacle may be designed with a comparatively small external diameter, which gives a receptacle that is easy to handle and easy to store.

According to another embodiment of the invention, the holding device comprises a helicoidally extending partition for mutual separation of the different spiral turns of the spiral-shaped path. Hereby, it will in a simple and efficient manner become possible to achieve mutual separation of the different spiral turns of the spiral-shaped path so that a catheter received in the storage space is prevented from coming into contact with itself along the spiral-shaped path.

According to another embodiment of the invention, the holding device comprises a sleeve rotatably arranged in the storage space, which sleeve is so arranged that a catheter that is pushed into the receptacle through said opening will come into contact with the inner side of the sleeve so as to thereby facilitate the pushing of the catheter into the storage space. By the friction between the catheter and the sleeve, the sleeve will rotate as the catheter is pushed into the storage space, whereby the frictional resistance during the insertion of the catheter into the storage space is considerably reduced.

According to another embodiment of the invention, the receptacle comprises one or several ventholes or drainage holes connected to the storage space. The drying is hereby expedited of a damp catheter which after use and possible subsequent cleaning has been inserted into the receptacle, which reduces the bacterial growth and makes possible a bacterial quantity on the catheter and in the storage space that decreases as the storage time increases. Holes of this type are also of advantage in connection with the cleaning of the interior of the receptacle, since they facilitate the discharge of cleaning agent and rinsing fluid from the storage space.

According to another embodiment of the invention, said storage space constitutes a first storage space of the receptacle, the receptacle comprising a second storage space that is separated from the first storage space. This second storage space may be used for storing for instance lubricant, wet wipes and other things that could be of use in connection with a catheterization.

According to another embodiment of the invention, the second storage space is connected to the first storage space so as to allow drying agent provided in the second storage space to absorb moisture from the first storage space. Hereby, it will in an efficient manner become possible to expedite the drying of a damp catheter which after use and possible subsequent cleaning has been inserted into the receptacle, which reduces the bacterial growth and makes possible a bacterial quantity on the catheter and in the storage space that decreases when the storage time increases.

Other preferred embodiments of the invention will appear from the dependent claims and the subsequent description.

The invention also relates to the use of an inventive receptacle for storing a urinary catheter or blood catheter or catheter for medicine delivery. The receptacle according to the invention is particularly advantageous with respect to the storing of a urinary catheter, since urinary catheterization has to be possible to be performed by the patient by his/her own.

BRIEF DESCRIPTION OF THE DRAWINGS

The invention will in the following be more closely described by means of embodiment examples, with reference to the appended drawings. It is shown in:

FIG. 1 a perspective view of a receptacle according to a first embodiment of the present invention, FIG. 2 a perspective view of a receptacle according to a second embodiment of the invention, FIG. 3 an exploded view of a receptacle according to a third embodiment of the invention, FIG. 4 a cross-sectional view of the receptacle according to FIG. 3, and FIG. 5 a perspective view of a receptacle according to a fourth embodiment of the invention.

Figure 3:
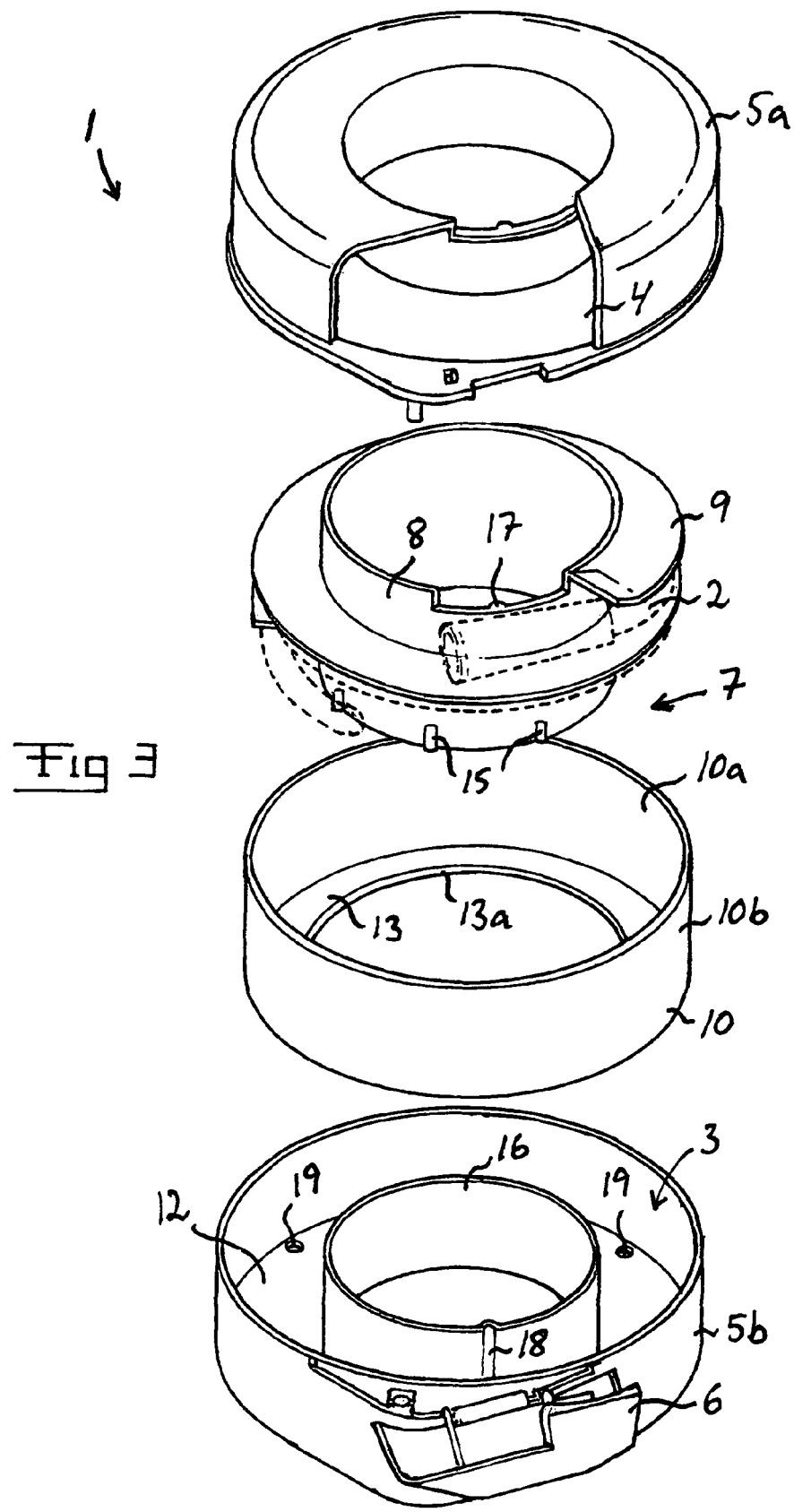

Corresponding details have in the different figures been designated with the same reference signs.

DESCRIPTION OF THE PREFERRED EMBODIMENTS

Different embodiments of a receptacle 1 according to the present invention for enclosing a catheter 2 before and after use thereof are shown in FIGS. 1-5. The receptacle 1 may be offered for sale together with a new and sterilized catheter 2 enclosed in the receptacle and used by the user as a portable storage and transport receptacle for the catheter. When the catheter 2 is to be used in order to perform a catheterization, the catheter is pulled out of the receptacle and may after the use be reinserted into the receptacle in order to be stored therein while waiting for either re-use in connection with a later catheterization or transfer to a suitable waste container.

The receptacle 1 comprises a storage space 3 designed to receive a catheter 2, and an opening 4 connected to the storage space, through which opening a catheter in its longitudinal direction is pushable into and pullable out of the storage space. The receptacle 1 has an outer casing 5 of self-supporting and preferably rather rigid material that encloses the storage space 3. The receptacle 1 is provided with a closing member 6, by means of which the storage space 3 is openable and reclosable. This closing member 6 is in its closed position (see FIG. 5) arranged to cover the opening 4 of the storage space and thereby prevent access to a catheter 2 received in the storage space 3, and to uncover the opening 4 in its open position (see FIGS. 1-3) and thereby allow access to a catheter 2 received in the storage space 3. The closing member 6 has suitably the form of a lid, which with advantage is hingedly attached to the outer casing 5, as illustrated in FIGS. 1-3 and 5. The lid 6 and the outer casing 5 may be formed in one single piece or the lid may constitute a separate part mounted to the outer casing. The lid 6 is shown in continuous lines in open position and in broken lines in closed position in FIGS. 1 and 2. The lid 6 could be provided with a seal that is broken the first time the lid is opened. An unbroken seal will indicate that a catheter 2 stored in the receptacle 1 is unused.

The receptacle 1 comprises one or several ventholes and/or drainage holes 19, which are connected to the storage space 3 and extends through the outer casing 5 in order to allow passage of air and liquid into and out of the storage space 3.

Figure 4:
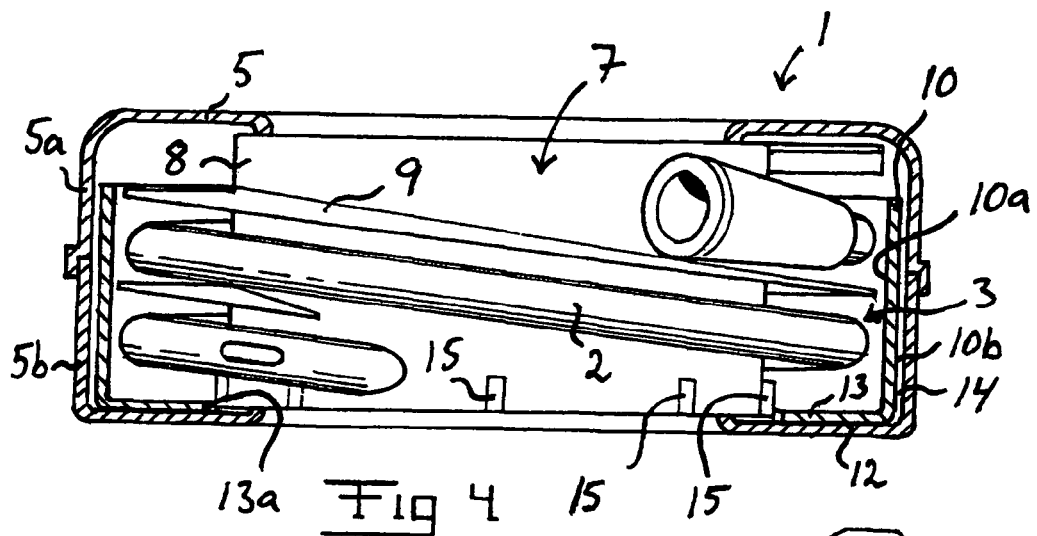

The receptacle 1 comprises a holding device 7 arranged in the storage space 3, which holding device is arranged to keep a catheter 2 inserted into the storage space in a spiral-shaped path under mutual separation of the different spiral turns of the spiral-shaped path so that a catheter is prevented from coming into contact with itself along the spiral-shaped path, as clearly illustrated in FIG. 4. The part of a catheter 2 received in the storage space 3 that extends along one spiral turn of the spiral-shaped path is consequently prevented from coming into contact with a part of the catheter extending along an adjacent spiral turn of the spiral-shaped path.

The holding device 7 is suitably arranged to keep a catheter inserted into the storage space 3 in a helicoidal path, which consequently implies that the catheter 2 in the storage space extends in several mutually superposed spiral turns, as illustrated in FIGS. 3 and 4. In the embodiment according to FIG. 1 and the embodiment according to FIGS. 3 and 4 the holding device 7 comprises a hub 8, about which the spiral-shaped path extends, and a helicoidally extending partition 9 for mutual separation of the different spiral turns of the spiral-shaped path. The partition 9 may extend continuously along the spiral-shaped path, as illustrated in FIGS. 3 and 4, or may in its longitudinal direction be divided into separate wall sections mutually separated by intermediate dividing gaps. The partition 9 forms a spiral-shaped channel for receiving a catheter and restricts the freedom of movement of a received catheter in directions perpendicular to the longitudinal direction of the catheter. In the illustrated examples, the partition 9 is attached to the hub 8. The holding device 7 could alternatively be constituted by an elongated tubular and spirally extending element arranged to internally receive a catheter, as illustrated in FIG. 2.

In the embodiment illustrated in FIGS. 3 and 4, the holding device 7 comprises a sleeve 10 rotatably arranged in the storage space 3, which sleeve is so arranged that a catheter that is pushed into the receptacle through the opening 4 will come into contact with the inner side 10a of the sleeve so as to thereby facilitate the pushing of the catheter into the storage space. The sleeve 10 is arranged to prevent the catheter 2 from being pressed against the inner side of the outer casing 5 during the insertion into the storage space 3. The sleeve 10 is arranged on the outside of the partition 9 and is rotatable in relation to this. In the illustrated example, the sleeve 10 rests against an internal bottom surface 12 of the outer casing 5 of the receptacle via a lower flange 13 of the sleeve. In this case the sleeve 10 is slidably mounted in the receptacle 1, said bottom surface 12 and flange 13 constituting mutual sliding surfaces. The sleeve 10 is suitably so arranged that there is an interspace 14 between its envelop surface 10b and the adjacent walls of the outer casing 5 of the receptacle, as illustrated in FIG. 4, which consequently implies that the outer diameter of the sleeve is somewhat smaller than the inner diameter of the outer casing. In the illustrated example, the sleeve 10 is kept in place laterally by the hub 8, which down in the lower part on its outer side is provided with protrusions 15 distributed in the circumferential direction, which protrusions form essentially point-shaped contact surfaces between the hub 8 and the inner edge 13a of the flange 13 of the sleeve. In the illustrated example, the hub 8 constitutes a part which is separate in relation to the outer casing 5 and which is attached on the outside of the tubular central section 16 of the outer casing 5. A guiding, here in the form of an axially extending protrusion 17 on the inner side of the hub and a corresponding groove 18 in said central section 16, is arranged to prevent mutual rotation between the hub 8 and the central section 16, i.e. prevent the hub 8 and the partition 9 attached thereon from rotating in relation to the outer casing 5.

In the illustrated embodiments, the outer casing 5 comprises an upper ring-shaped part 5a and a lower ring-shaped part 5b, which are assembled to each other. These ring-shaped parts 5a, 5b together delimit a ring-shaped storage space 3 for receipt of a catheter. The receptacle 1 is designed as a portable box, which in the illustrated examples has an essentially circular external shape. However, the receptacle 1 could alternatively have another external shape if so considered suitable. The receptacle is ring-shaped in the embodiment illustrated in FIG. 1 and in the embodiment illustrated in FIGS. 3 and 4.

Figure 5:
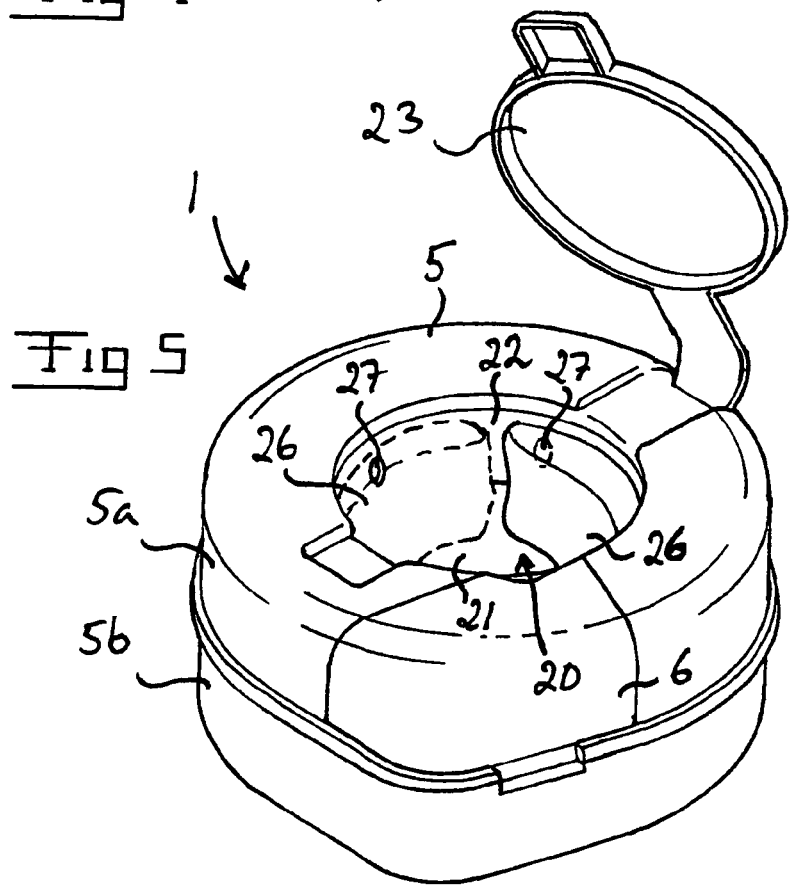

In the embodiments illustrated in FIGS. 2 and 5, the receptacle comprises a first storage space 3 of the type described above for storage of a catheter 2, and a second storage space 20 that is separated from the first storage space 3. The first storage space 3 is here ring-shaped and the second storage space 20 is encircled by the first storage space. The second storage space 20 is at the bottom delimited by a bottom 21 and laterally delimited from the first storage space 3 by a cylinder-shaped wall 22. The receptacle 1 is provided with a closing member 23, by means of which the second storage space 20 is openable and reclosable. This closing member 23 is in its closed position (indicated by broken lines in FIG. 2) arranged to cover the upper opening of the storage space and thereby prevent access to the storage space 20, and to uncover the upper opening of the storage space in its open position and thereby allow access to the storage space 20. The closing member 23 has suitably the form of a lid, which with advantage is hingedly attached to the outer casing 5, as illustrated in FIGS. 2 and 5. The lid 23 and the outer casing 5 may be formed in one single piece or the lid may constitute a separate part mounted to the outer casing. The second storage space 20 may for instance be utilized for storing lubricant, which is advantageous to use in connection with insertion of a urinary catheter into a urethra. The lubricant is suitably enclosed in a suitable package 24, which has such a size that it can be stored in the second storage space 20. The second storage space 20 may also be utilized for storing wet wipes 25 or other things.

In the embodiment illustrated in FIG. 5, drying agent 26 is arranged in the second storage space 20, the second storage space 20 being connected to the first storage space 3 so as to allow the drying agent 26 to absorb moisture from the first storage space 3. In the illustrated example, the second storage space 20 is connected to the first storage space 3 via through holes 27 in the wall 22.

The receptacle 1 comprises with advantage a sterilization indicator 30 (see FIGS. 1 and 2), which is arranged to indicate whether the receptacle 1 has been subjected to a sterilization process. The sterilization indicator 30 may for instance be arranged to change colour when the receptacle 1 is subjected to a sterilization process.

The receptacle 1 may be provided with a plate or label 31 (see FIGS. 1 and 2), by means of which the receptacle can be marked in a desired manner.

The receptacle 1 is suitably made of plastic material, preferably polypropylene. However, also other materials are possible.

The invention is of course not in any way limited to the preferred embodiments described above. On the contrary, several possibilities to modifications thereof should be apparent to a person skilled in the art without departing from the basic idea of the invention as defined in the appended claims.

The invention claimed is:

1. A receptacle for a catheter, which receptacle (1) comprises a storage space (3) designed for receiving a catheter, and an opening (4) connected to the storage space, through which opening a catheter in its longitudinal direction is pushable into and pullable out of the storage space (3), wherein the receptacle (1) comprises a holding device (7) arranged in the storage space (3), which holding device is arranged to keep a catheter inserted into the storage space (3) in a spiral-shaped path under mutual separation of the different spiral turns of the spiral-shaped path so that the catheter is prevented from coming into contact with itself along the spiral-shaped path, the holding device (7) is arranged to keep a catheter inserted into the storage space (3) in a helicoidal path, and the holding device (7) comprises a sleeve (10) rotatably arranged in the storage space (3), which sleeve is so arranged that a catheter that is pushed into the receptacle via said opening (4) comes into contact with the inner side (10a) of the sleeve to thereby facilitate the pushing of the catheter into the storage space.

2. A receptacle according to claim 1, wherein the holding device (7) comprises a hub (8), about which the spiral-shaped path extends.

3. A receptacle according to claim 2, wherein the holding device (7) comprises a helicoidally extending partition (9) for mutual separation of the different spiral turns of the spiral-shaped path.

4. A receptacle according to claim 3, wherein the partition (9) is attached to the hub (8).

5. A receptacle according to claim 3, wherein the sleeve (10) is arranged on the outside of the partition (9) and is rotatable in relation to the partition.

6. A receptacle according to claim 1, wherein the receptacle (1) is provided with a closing member (6) by which the storage space (3) is openable and reclosable.

7. A receptacle according to claim 6, wherein the closing member (6) is in the form of a hinged lid.

8. A receptacle according to claim 1, wherein the receptacle is designed as a portable box.

9. A receptacle according to claim 8, wherein the receptacle is designed with a substantially circular external shape.

10. A receptacle according to claim 1, wherein the receptacle (1) is ring-shaped.

11. A receptacle according to claim 1, wherein the receptacle (1) comprises at least one vent or drainage hole (19) connected to the storage space (3).

12. A receptacle according to claim 11, comprising several vent or drainage holes (19).

13. A receptacle according to claim 1, wherein the storage space (3) is ring-shaped.

14. A receptacle according to claim 1, wherein said storage space (3) constitutes a first storage space of the receptacle (1), and the receptacle comprises a second storage space (20) that is separated from the first storage space.

15. A receptacle according to claim 14, wherein the first storage space (3) is ring-shaped and the second storage space (20) is encircled by the first storage space.

16. A receptacle according to claim 14, wherein the second storage space (20) is connected to the first storage space (3) to allow drying agent provided in the second storage space (20) to absorb moisture from the first storage space.

17. A receptacle according to claim 14, wherein the receptacle (1) is provided with a closing member (23) by which the second storage space (20) is openable and reclosable.

18. A receptacle according to claim 17, wherein the closing member (23) is in the form of a hinged lid.

19. A receptacle (1) according to claim 1, structured and arranged for storing a urinary catheter or blood catheter or catheter for medicine delivery.

* * * * *